United States Patent [19]
Zink

[11] Patent Number: 4,973,712
[45] Date of Patent: Nov. 27, 1990

[54] 2-ARALKYLAMINOFLUORANS, THEIR PREPARATION AND THE USE THEREOF IN RECORDING MATERIALS

[75] Inventor: Rudolf Zink, Therwil, Switzerland

[73] Assignee: Ciba-Geigy Corporation, Ardsley, N.Y.

[21] Appl. No.: 312,788

[22] Filed: Feb. 21, 1989

[30] Foreign Application Priority Data
Mar. 1, 1988 [CH] Switzerland .................... 763/88

[51] Int. Cl.⁵ ............................................. C07D 307/88
[52] U.S. Cl. ...................................... 549/265; 546/15; 548/407
[58] Field of Search ........................ 546/15; 548/407; 549/265

[56] References Cited
U.S. PATENT DOCUMENTS
4,007,195 2/1977 Garner .................................. 546/15
4,603,202 7/1986 Mayer ................................ 548/407

FOREIGN PATENT DOCUMENTS
8345088 3/1983 Japan .

*Primary Examiner*—Robert A. Wax
*Attorney, Agent, or Firm*—Kevin T. Mansfield; George R. Dohmann

[57] ABSTRACT

Novel 2-aralkylaminofluorans of formula

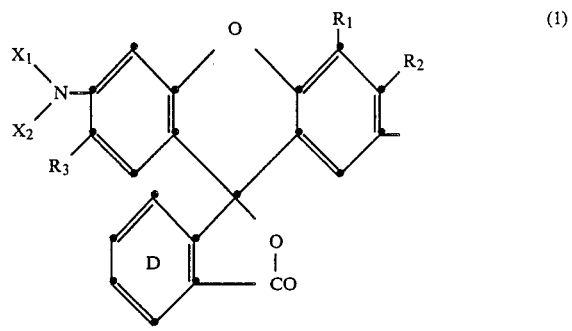

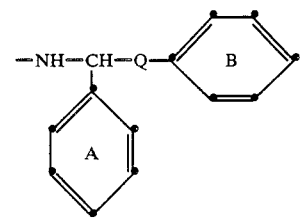

wherein
Q is —CH$_2$—, —CH$_2$—O— or —CO—,
R$_1$, R$_2$ and R$_3$ are each independently of one another hydrogen, halogen, lower alkyl or lower alkoxy,
X$_1$ and X$_2$ are each independently of the other hydrogen, alkyl which is unsubstituted or substituted by halogen, hydroxy, cyano, tetrahydrofuryl or lower alkoxy, or ar cycloalkyl or benzyl or phenyl, each unsubstituted or substituted by halogen, cyano, nitro, lower alkyl, lower alkoxy or lower alkoxycarbonyl; or
—NX$_1$X$_2$ is a 5- 6-membered heterocyclic radical, and wherein the benzene rings A and B are independently of the other unsubstituted or substituted by halogen, cyano, lower alkyl, lower alkoxy, lower alkylthio, lower alkoxycarbonyl or trifluoromethyl, and the ring D is unsubstituted or substituted by halogen, nitro, lower alkyl, lower alkoxy, lower alkylthio, amino, mono-lower alkylamino or di-lower alkylamino.

The fluorans are particularly suitable color formers for use in pressure-sensitive or heat-sensitive recording materials and develop strong green, greenish-blue, grey or black colored images.

6 Claims, No Drawings

2-ARALKYLAMINOFLUORANS, THEIR PREPARATION AND THE USE THEREOF IN RECORDING MATERIALS

The present invention relates to novel 2-aralkylaminofluorans, to their preparation, and to the use thereof as colour formers in pressure-sensitive or heat-sensitive recording materials.

The 2-aralkylaminofluorans of this invention have the general formula

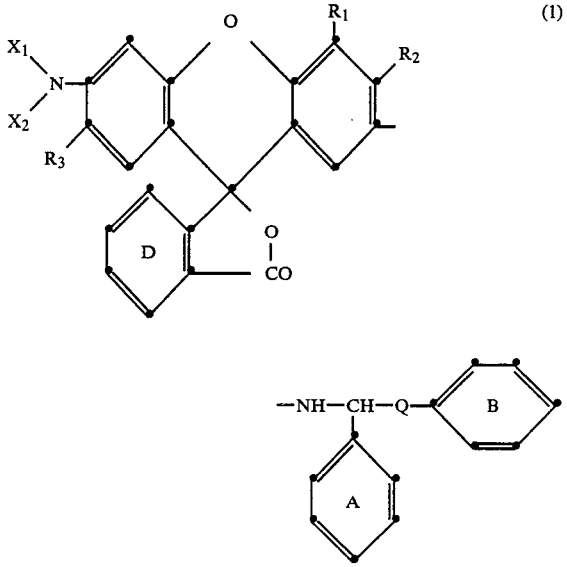

wherein

Q is —$CH_2$—, —$CH_2$—O— or —CO—, $R_1$, $R_2$ and $R_3$ are each independently of one another hydrogen, halogen, lower alkyl or lower alkoxy, $X_1$ and $X_2$ are each independently of the other hydrogen, alkyl of not more than 12 carbon atoms which is unsubstituted or substituted by halogen, hydroxy, cyano, tetrahydrofuryl or lower alkoxy, or are cycloalkyl or benzyl or phenyl, each unsubstituted or substituted by halogen, cyano, nitro, lower alkyl, lower alkoxy or lower alkoxycarbonyl; or —$NX_1X_2$ is a 5- or 6-membered, preferably saturated, heterocyclic radical, and wherein the benzene rings A and B are each independently of the other unsubstituted or substituted by halogen, cyano, lower alkyl, lower alkoxy, lower alkylthio, lower alkoxycarbonyl or trifluoromethyl, and the ring D is unsubstituted or substituted by halogen, nitro. lower alkyl, lower alkoxy, lower alkylthio, amino, mono-lower alkylamino or di-lower alkylamino.

In the definition of the radicals of the fluorans, lower alkyl, lower alkoxy and lower alkylthio denote those groups or moieties which contain from 1 to 5, preferably from 1 to 3, carbon atoms. Examples of such groups are: methyl, ethyl, n-propyl, isopropyl, n-butyl, sec-butyl, tert-butyl, amyl or isoamyl; methoxy, ethoxy, isopropoxy or tert-butoxy; and methylthio, ethylthio, propylthio or butylthio.

Halogen is typically fluoro, bromo, or, preferably, chloro.

Q is preferably —CO— or also —$CH_2$—.

$R_1$, $R_2$ and $R_3$ are preferably hydrogen, methyl, methoxy, bromo or chloro.

Alkyl groups $X_1$ and $X_2$ may be in straight-chain or branched-chain configuration and are, for example, methyl, ethyl, n-propyl, isopropyl, n-butyl, sec-butyl, tert-butyl, 1,1,3,3-tetramethylbutyl, amyl, isoamyl, n-hexyl, 2-ethylhexyl, n-heptyl, n-octyl, isooctyl, n-nonyl, isononyl or n-dodecyl.

Substituted alkyl groups $X_1$ and $X_2$ are preferably cyanoalkyl, haloalkyl, hydroxyalkyl or alkoxyalkyl, each preferably containing in all 2 to 6 carbon atoms. Examples of such groups are: $\beta$-cyanoethyl, $\beta$-chloroethyl, $\gamma$-chloropropyl, $\beta$-hydroxyethyl, $\gamma$-hydroxypropyl, $\beta$-methoxyethyl, $\beta$-ethoxyethyl or $\gamma$-methoxypropyl. A further substituted-alkyl radical is tetrahydrofurfuryl.

$X_1$ and $X_2$ as cycloalkyl are typically cyclopentyl, cycloheptyl or, preferably, cyclohexyl. The cycloalkyl radicals may contain one or more $C_1$–$C_4$alkyl groups, preferably methyl groups, and have in all 5 to 10 carbon atoms.

Preferred substituents of the benzyl and phenyl moieties of the radicals X are, for example, halogen, cyano, methyl, methoxy or carbomethoxy. Examples of such araliphatic and aromatic radicals are methylbenzyl, 2,4- or 2,5-dimethylbenzyl, chlorobenzyl, dichlorobenzyl, cyanobenzyl, tolyl, xylyl, 2,6-dimethylphenyl, chlorophenyl, methoxyphenyl or carbomethoxyphenyl.

Heterocyclic radicals —$NX_1X_2$ are, for example, pyrrolidino, piperidino, pipecolino, morpholino, thiomorpholino or piperazino, for example N-methylpiperazino. Preferred saturated heterocyclic radicals —$NX_1X_2$ are pyrrolidino, piperidino or morpholino.

The substituents $X_1$ and $X_2$ are preferably cyclohexyl, tolyl, xylyl, benzyl, cyano-lower alkyl, for example $\beta$-cyanoethyl or, preferably, lower alkyl such as methyl, ethyl, n-propyl, isopropyl, n-butyl or isoamyl. —$NX_1X_2$ is preferably also pyrrolidinyl, tetrahydrofurfurylamino or N-$C_1$–$C_5$-alkyl-N-tetrahydrofurfurylamino.

The benzene rings A and B are preferably unsubstituted. If they do contain substituents, then these are preferably methyl, chloro, cyano, trifluoromethyl, methoxy or carbomethoxy.

The ring D is also preferably not further substituted, but if it does contain substituents, then these are preferably halogen, nitro or di-lower alkylamino.

Useful 2-aralkylaminofluorans are those of formula

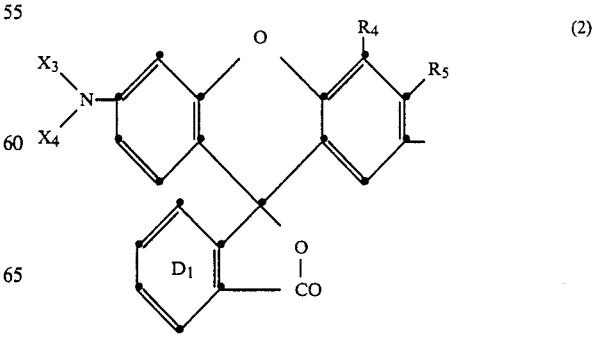

(2)

-continued

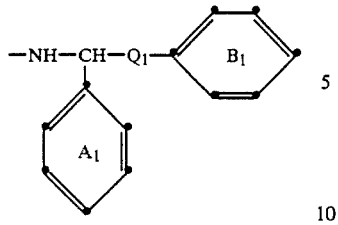

wherein $Q_1$ is —CH$_2$— or, preferably, —CO—, $R_4$ and $R_5$ are each independently of the other hydrogen, halogen or lower alkyl, $X_3$ is $C_1$-$C_6$alkyl, $C_5$-$C_6$cycloalkyl, benzyl, phenyl or phenyl which is substituted by halogen, $C_1$-$C_4$alkyl or $C_1$-$C_4$alkoxy, $X_4$ is $C_1$-$C_6$alkyl or benzyl, or —$NX_3X_4$ is pyrrolidinyl, piperidinyl, morpholinyl or also tetrahydrofurfurylamino or N-ethyl-N-tetrahydrofurfurylamino, and wherein the benzene rings $A_1$ and $B_1$ are each independently of the other unsubstituted or substituted by halogen, lower alkyl or lower alkoxy, and the ring $D_1$ is unsubstituted or substituted by halogen.

Among the compounds of formula (2), preferred fluorans are those in which $X_3$ and $X_4$ are $C_1$-$C_4$ alkyl, $R_4$ and $R_5$ are hydrogen, methyl or chloro, and the rings $A_1$, $B_1$ and $D_1$ are unsubstituted.

Particularly interesting fluorans are those of formula

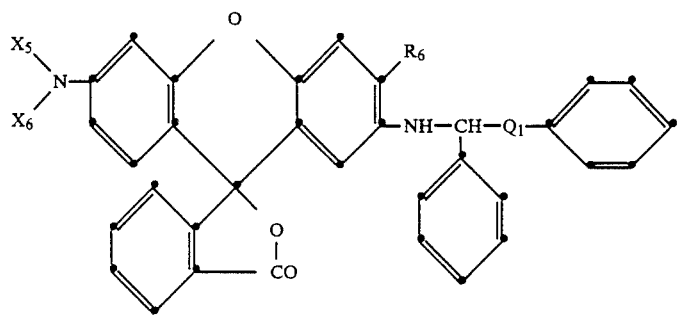

wherein $Q_1$ is —CH$_2$ or, preferably, —CO—, $R_6$ is hydrogen or methyl, $X_5$ is $C_1$-$C_4$alkyl, cyclohexyl or tolyl, and $X_6$ is $C_1$-$C_4$alkyl.

The 2-aralkylaminofluorans of formulae (1) to (3) are prepared by reacting a fluoran of formula

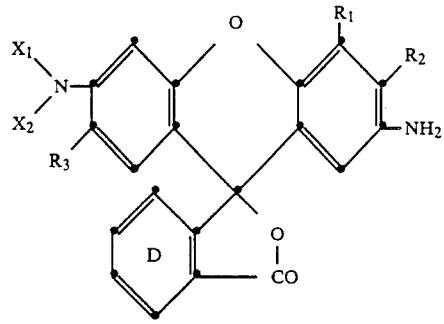

wherein $R_1$, $R_2$, $R_3$, $X_1$, $X_2$ and D have the given meanings, with an aralkylating agent of formula

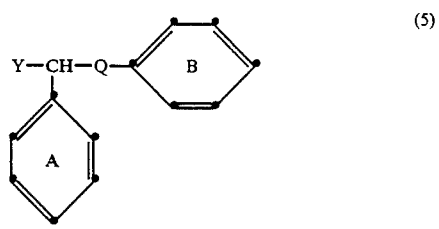

wherein A, B and Q have the given meanings, and Y is halogen, alkylsulfonyloxy or arylsulfonyloxy. Y is preferably chloro, phenylsulfonyloxy, bromophenylsulfonyloxy, nitrophenylsulfonyloxy or, most preferably, p-tolylsulfonyloxy.

The required starting 2-aminofluorans of formula (4) can be prepared in known manner by reacting a compound of formula

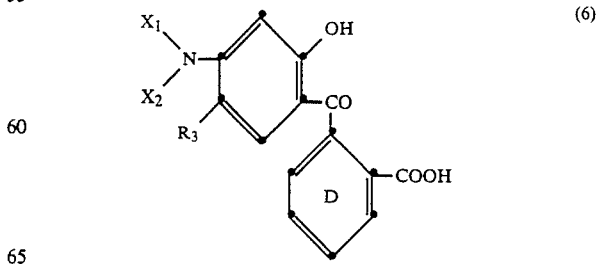

wherein $X_1$, $X_2$, $R_3$ and D have the given meanings, with an aminophenol derivative of formula

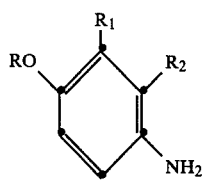

(7)

wherein $R_1$ and $R_2$ have the given meanings and R is hydrogen or methyl, in the presence of a condensing agent.

The reaction of the fluoran of formula (4) with the aralkylating agent of formula (5) is conveniently carried out at elevated temperature, preferably in the range from 70° to 120° C., and in the presence of an acid acceptor.

Examples of suitable acid acceptors are alkali metal hydroxides, alkaline earth metal hydroxides, alkali metal bicarbonates, alkali metal carbonates or tertiary nitrogen bases, for example pyridine, N-methylpiperidine or trialkylamines, or also mixtures of these compounds. Preferred acid acceptors are sodium bicarbonate and potassium carbonate.

The reaction is conveniently carried out in an organic solvent, for example methanol, ethanol, isopropanol, methyl cellosolve, ethyl cellosolve, acetone, methyl ethyl ketone, methyl isopropyl ketone, dimethyl formamide or, preferably, in an aromatic solvent such as benzene, toluene, xylene, a chlorobenzene such as dichlorobenzene or trichlorobenzene, or nitrobenzene. Preferred solvents are toluene and xylene.

The preferred aralkylating agent of formula (5) is desyl chloride, desyl benzenesulfonate or desyl p-toluenesulfonate.

By means of an alternative process, the 2-aralkylaminofluorans of formulae (1) to (3), wherein Q is —CO—, can be prepared by reacting a 2-aminofluoran of formula (4) with a compound of formula (8)

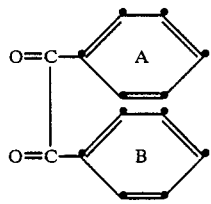

(8)

wherein A and B have the given meanings, and reducing the reaction product of formula wherein A, B, D, $R_1$, $R_2$, $R_3$, $X_1$ and $X_2$ have the given meanings.

The reaction of the fluoran of formula (4) with the keto compound of formula (8) can be carried out in the temperature range from 10° to 150° C. An organic solvent may be used as reaction medium. It is convenient to add an acid catalyst. Examples of such catalysts are lower aliphatic carboxylic acids or the anhydrides thereof such as acetic anhydride, as well as zinc chloride, sulfuric acid, phosphoric acid or phthalic acid.

Examples of suitable solvents are cycloaliphatic or aromatic hydrocarbons such as cyclohexane, benzene, toluene or xylene; chlorinated hydrocarbons such as chloroform, ethylene chloride or chlorobenzene; ethers such as diethyl ether or glycol dimethyl ether; cyclic ethers such as dioxane or tetrahydrofuran; as well as dimethyl formamide, diethyl formamide, dimethyl sulfoxide, acetic acid or acetonitrile.

The reduction is conveniently carried out in an ether such as diethyl ether, tetrahydrofuran or dioxane, in the temperature range from 20° to 120° C., preferably at the boiling temperature of the solvent employed.

Examples of suitable reducing agents are methal hydrides such as lithium aluminium hydride or sodium borohydride. The reduction may also be carried out catalytically with hydrogen in the presence of a metal catalyst such as platinum, Raney nickel or palladium on carbon.

A further process for the preparation of the fluorans of formulae (1) to (3) comprises reacting a fluoran of formula (4) with a carbinol of formula

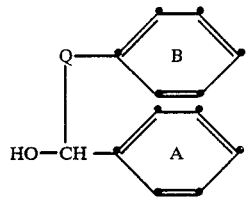

(10)

wherein A, B and Q have the given meanings.

The reaction of the fluoran of formula (4) with the carbinol of formula (10) is conveniently carried out in a polar organic solvent, preferably in a lower aliphatic alcohol such as methanol, ethanol or isopropanol, or in an ether such as tetrahydrofuran, and preferably in the presence of an acid catalyst. Although the condensation may be effected at room temperature (20° to 25° C.), a higher temperature up to reflux temperature is expedient, the preferred range being from 40° to 100° C. Suitable acid catalysts are inorganic acids, for example hy-

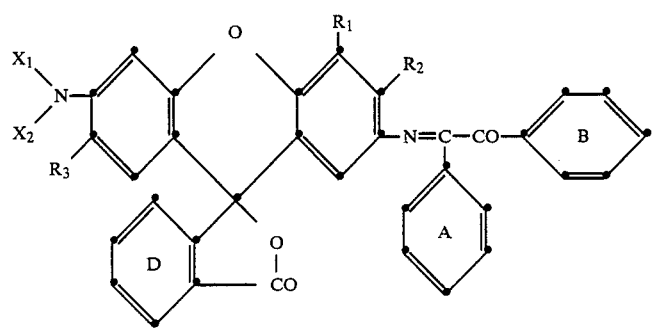

(9)

drochloric acid, sulfuric acid, phosphoric acid or perchloric acid, as well as lower aliphatic carboxylic acids such as formic acid or acetic acid.

The compounds of this invention contain at least two asymmetric carbon atoms or centres of chirality and are in the form of mixtures of diastereoisomers. The individual diastereoisomer components (A and B) can be isolated by column chromatography over silica gel or by crystallisation, and can be clearly distinguished on the basis of their physicochemical properties. The eluants used are principally toluene, ethyl acetate, methanol, isopropanol, chloroform and mixtures thereof.

The fluorans of formula (1) to (3) are normally colourless or, at most, faintly coloured. When these colour formers are brought into contact with a preferably acid developer, i.e. an electron acceptor, then, depending on the meaning of Q and on the developer employed, they develop strong violet, green, greenish-blue, grey-green, grey or black coloured images which are particularly fast to sublimation.

The fluorans of formulae (1) to (3) are also very useful when combined with one or more other known colour formers, for example 3,3-(bisaminophenyl)phthalides, 3-indolyl-3-aminophenylazaphthalides, 3,3-(bisindolyl)phthalides, 3,6-bis(alkoxy)fluorans, 3-aminofluorans, 6-dialkylamaino-2-dibenylaminofluorans, 6-dialkylamino-3-methyl-2-arylaminofluorans, leucoauramines, spiropyranes, spirodipyranes, chromenoindoles, chromenopyrazoles, phenoxazines, phenothiazines, quinazolines, rhodamine lactams, carbazolylmethanes or other triarylmethaneleuco dyes, to give grey or black coloured images.

The fluorans of formulae (1) to (3) develop on activated clays as well as on phenolic substrates an excellent colour intensity. They are especially suitable for use as rapidly developing colour formers in a heat-sensitive, or especially in a pressure-sensitive, recording material which can also be a copying material. They are distinguished by the property of being pH-stable, light-fast, and of being readily soluble in the capsule oils. After exposure on a CB sheet, they exhibit a slight decrease in colour strength (CB decline).

A pressure-sensitive material comprises, for example, at least one pair of sheets which contain at least one colour former of formulae (1) to (3), dissolved in an organic solvent, and an electron acceptor as developer.

Typical examples of such developers are activated clays such as attapulgite, acid clay, bentonite, montmorillonite, activated clay, for example acid-activated bentonite or montmorillonite, and also zeolith, halloysite, silica, alumina, aluminium sulfate, aluminium phosphate, zinc chloride, zinc nitrate, zirconium dioxide, activated kaolin or any clay. Suitable developers are also acidic organic compounds, for example unsubstituted or ring-substituted phenols, resorcinols, salicylic acids, e.g. 3,5-bis($\alpha,\alpha$-dimethylbenzyl)salicylic acid or 3,5-bis($\alpha$-methylbenzyl)salicylic acid, or salicylates and their metal salts, e.g. zinc salts, or an acidic polymer, for example a phenolic polymer, an alkylphenol acetylene resin, a maleic acid/rosin resin or a partially or completely hydrolysed polymer of maleic acid and styrene, ethylene or vinyl methyl ether, or carboxymethylene. Mixtures of these monomers and polymers can also be used. Particularly preferred developers are acid-activated bentonite, zinc salicylates or the condensates of p-substituted phenols with formaldehyde. These last mentioned compounds may also be modified with zinc.

The developers may also be used in admixture with other basically inert or almost inert pigments or with other auxiliaries such as silica gel or UV absorbers, e.g. 2-(2-hydroxyphenyl)benzotriazoles. Examples of such pigments are: talcum, titanium dioxide, alumina, aluminium hydroxide, zinc oxide, chalk, clays such as kaolin, as well as organic pigments, e.g. urea/formaldehyde condensates (BET surface area: 2–75 $m^2/g$) or melamine/formaldehyde condensates.

The colour former effects a coloured marking at those points where it comes into contact with the electron acceptor. To prevent the colour formers contained in the pressure-sensitive recording material from being activated prematurely, they are usually separated from the electron acceptor. This separation can conveniently be accomplished by incorporating the colour formers in foam-like, sponge-like or honeycomb-like structures. The colour formers are preferably encapsulated in microcapsules, which can normally be ruptured by pressure.

When the capsules are ruptured by pressure, for example with a pencil, the colour former solution is transferred to an adjacent sheet coated with an electron acceptor to produce a coloured image thereon. This colour results from the dye thereby formed, which is absorbed in the visible range of the electromagnetic spectrum.

The colour formers are preferably encapsulated in the form of solutions in organic solvents. Examples of suitable solvents are preferably non-volatile solvents, for example a halogenated paraffin such as chloroparaffin, or a halogenated diphenyl such as monochlorodiphenyl or trichlorodiphenyl, and also tricresyl phosphate, di-n-butyl phthalate, dioctyl phthalate, trichlorobenzene, trichloroethyl phosphate, an aromatic ether such as benzylphenyl ether, a hydrocarbon oil such as paraffin or kerosene, an alkylated derivative, e.g an isopropyl, isobutyl, sec- or tert-butyl derivative, of diphenyl, diphenylalkane, naphthalene or terphenyl; dibenzyl toluene, terphenyl, partially hydrogenated terphenyl, a benzylated xylene, or other chlorinated or hydrogenated, condensed aromatic hydrocarbons. Mixtures of different solvents, especially mixtures of paraffin oils or kerosene and diisopropylnaphthalene or partially hydrogenated terphenyl, are often used in order to achieve an optimum solubility for the colour formation, a rapid and strong coloration, and a viscosity which is advantageous for the microencapsulation. When encapsulated, the fluorans of this invention are distinguished by exceedingly good pH stability, e.g. in the range from 4 to 10.

The capsules walls can be formed evenly around the droplets of the colour former solution by coacervation; and the encapsulating material is as described e.g. in U.S. Pat. No. 2,800,457. The capsules can also be formed preferably from an aminoplast or a modified aminoplast by polycondensation, as described in British patent specifications 989 264, 1 156 725, 1 301 052 and 1 355 124. Also suitable are microcapsules which are formed by interfacial polymerisation, e.g. capsules formed from polyester, polycarbonate, polysulfonamide, polysulfonate, but in particular from polyamide or polyurethane.

The microcapsules containing the colour formers of formulae (1) to (3) can be used for the production of a wide range of known kinds of pressure-sensitive copying materials. The various systems differ substantially from one another in the arrangement of the capsules and of the colour reactants, and in the support. A preferred arrangement is that in which the encapsulated colour former is in the form of a layer on the back of a transfer sheet and the developer is in the form of a layer on the face of a receiver sheet.

Another arrangement of the components is that wherein the microcapsules containing the colour former and the developer are in or on the same sheet, in the form of one or more individual layers, or are present in the paper pulp.

The capsules are preferably secured to the support by means of a suitable adhesive. As paper is the preferred support, these adhesives are principally paper-coating agents, for example gum arabic, polyvinyl alcohol, hydroxymethylcellulose, casein, methyl cellulose, dextrin, starch or starch derivatives or polymer latices. These last mentioned substances are e.g. butadiene/styrene copolymers or acrylic homopolymers or copolymers.

The paper employed comprises not only normal paper made from cellulose fibres, but also paper in which the cellulose fibres are replaced (partially or completely) by synthetic polymers.

The compounds of formulae (1) to (3) can also be used as colour formers in a thermoreactive recording material. This recording material usually contains at least one carrier, one colour former, one electron acceptor and, in some cases, also a binder and/or wax. If desired, the recording material may also contain activators or sensitiser.

Thermoreactive recording systems comprise, for example, heat-sensitive recording or copying materials and papers. These systems are used e.g. for recording information, for example in electronic computers, teleprinters or telewriters, or in recording and measuring instruments, e.g. electrocardiographs. The image (mark) formation can also be effected manually with a heated pen. Laser beams can also be used to produce heat-induced marks.

The thermoreactive recording material can be composed such that the colour former is dispersed or dissolved in one binder layer and the developer is dissolved or dispersed in the binder in a second layer. An alternative method comprises dispersing both the colour former and the developer in one layer. By means of heat the binder is softened at specific areas and the colour former comes into contact with the electron acceptor at those points where heat is applied, whereupon the desired colour develops at once.

Suitable developers are the same electron acceptors as are used in pressure-sensitive papers. Examples of developers are the previously mentioned clays and phenolic resins, or also the phenolic compounds described e.g. in German Offenlegungsschrift 1 251 348, for example 4-tert-butylphenol, 4-phenylphenol, methylene-bis(p-phenylphenol), 4-hydroxydiphenyl ether, α-naphthol, β-naphthol, methyl 4-hydroxybenzoate or benzyl 4-hydroxybenzoate, 4-hydroxydiphenylsulfone, 2,4-dihydroxydiphenylsulfone, 4'-hydroxy-4-methyldiphenylsulfone, 4'-hydroxy-4-isopropoxydiphenylsulfone, 4-hydroxyacetophenone, 2,2'-dihydroxydiphenyl, 4,4'-cyclohexylidenediphenol, 4,4'-isopropylidenediphenol, 4,4'-isopropylidene-bis(2-methylphenol), an antipyrine complex of zinc thiocyanate, a pyridine complex of zinc thiocyanate, 4,4'-bis(4-hydroxyphenyl)valeric acid, hydroquinone, pyrogallol, phloroglucinol, p-, m- and o-hydroxybenzoic acid, gallic acid, 1-hydroxy-2-naphthoic acid, as well as boric acid or organic, preferably aliphatic, dicarboxylic acids, for example tartaric acid, oxalic acid, maleic acid, citric acid, citraconic acid or succinic acid.

Fusible, film-forming binders are preferably used for the preparation of the thermoreactive recording material. These binders are normally water-soluble, whereas the fluorans and the developer are sparingly soluble or insoluble in water. The binder should be able to disperse and fix the colour former and the developer at room temperature.

When heat is applied, the binder softens or melts, so that the colour former comes in contact with the developer and a colour is able to form. Examples of binders which are soluble, or at least swellable, in water are e.g. hydrophilic polymers such as polyvinyl alcohol, polyacrylic acid, hydroxyethylcellulose, methyl cellulose, carboxmethylcellulose, polyacrylamide, polyvinyl pyrrolidone, carboxylated butadiene/styrene copolymers, gelatin, starch, or etherified corn starch.

If the colour former and the developer are in two separate layers, it is possible to use water-insoluble binders, i.e. binders which are soluble in non-polar or only weakly polar solvents, for example natural rubber, synthetic rubber, chlorinated rubber, alkyd resins, polystyrene, styrene/butadiene copolymers, polymethylacrylates, ethyl cellulose, nitrocellulose or polyvinyl carbazole. The preferred arrangement, however, is that in which the colour former and the developer are contained in one layer in a water-soluble binder.

The thermoreactive coatings may contain further modifiers. To improve the degree of whiteness, to facilitate the printing of papers, and to prevent the heated pen from sticking, the coatings may contain e.g. talcum, titanium dioxide, zinc oxide, aluminium hydroxide, calcium carbonate (e.g. chalk), clays or also organic pigments, for example urea/formaldehyde polymers. In order to effect the colour formation only within a limited temperature range, it is possible to add substances such as urea, thiourea, diphenyl thiourea, acetamide, acetanilide, bis(stearoyl)ethylenediamide, benzosulfanilide, stearamide, phthalic anhydride, metal stearates such as zinc stearate, dimethyl terephthalate, phthalonitrile or other suitable fusible products which induce the simultaneous melting of the colour former and the developer. Thermographic recording materials preferably contain waxes, e.g. carnauba wax, montan wax, paraffin wax, polyethylene wax, condensates of higher fatty acid amides and formaldehyde, or condensates of higher fatty acids and ethylenediamine.

A further utility of the compounds of formulae (1) to (3) is the production of a coloured image with the photocurable microcapsules described in German Offenlegungsschrift 3 247 488.

The invention is illustrated by the following Examples, in which percentages are by weight, unless otherwise indicated.

EXAMPLE 1

(a) 11.6 g of 2-amino-6-diethylaminofluoran are partially dissolved at 25° C. in 50 ml of toluene. With stirring, 6.3 g of benzil and 0.3 g of 96% sulfuric acid are added. The reaction mixture is kept for 30 hours under reflux and the water of reaction is removed via a water separator. The reaction mixture is subsequently neutralised with aqueous ammonia. The toluene phase is then separated and concentrated. After addition of isopropanol, the precipitate so obtained is isolated by filtration and dried, affording 15.6 g of a compound of formula

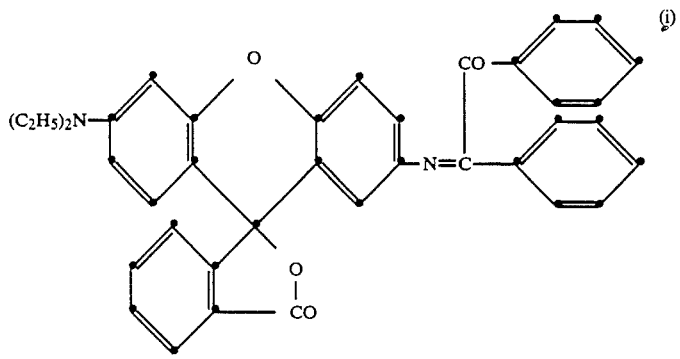

The compound of formula (i) has a melting point of 225°–227° C. after recrystallisation from toluene/petroleum ether. The compound of formula (i) develops a red image immediately on acid clay.

(b) 4.4 g of the compound of formula (i) are hydrogenated in 100 ml of dioxane with 1.4 g of 5% Pt/C at 15°–20° C. in 2¼ hours with 214 ml of hydrogen. The catalyst and the solvent are removed and the product is dried, affording 4.1 g of a fluoran of formula

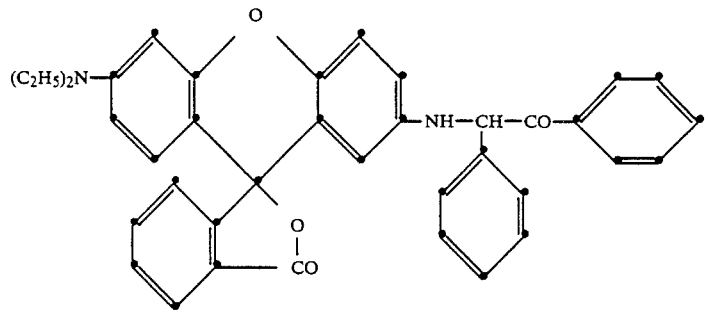

This compound is a mixture of diastereoisomeres which is separated by column chromatography over silica gel with toluene and 5% ethyl acetate into the individual diastereoisomer components A ($R_f$=0.57) and B ($R_f$=0.64).

Component A has a melting point of 176°–177° C. after recrystallisation from toluene/isopropyl alcohol. It develops a violet-grey image immediately on acid-modified clay. On phenolic resin paper it develops a greenish-grey image.

Component B has a melting point of 169°–171° C. after recrystallisation from toluene/isopropyl alcohol. Component B develops a reddish-green image immediately on acid-modified clay. On phenolic resin paper it develops a grey image.

EXAMPLE 2

7.7 g of 2-amino-6-diethylaminofluoran are stirred in 30 ml of xylene with 2.8 g of potassium carbonate and 7.3 g of desyl p-toluenesulfonat [J. Am. Chem. Soc. 73. (1951), 2635] for 18 hours at 80° C. The mixture of diastereoisomers of formula (11) present in the reaction solution is separated into the diastereoisomer components A and B by column chromatography as described in Example 1.

EXAMPLE 3

With stirring, 4.2 g of benzoin and 0.2 g of 96% sulfuric acid are added to 8.5 g of 2-amino-6-diethylaminofluoran in 100 ml of isopropyl alcohol. The mixture is kept for 4 hours under reflux, then neutralised with aqueous ammonia and cooled to room temperature. The precipitate is isolated by filtration, treated with 100 ml of 1N hydrochloric acid at 40°–45° C., isolated by filtration once more and taken up in toluene. The toluene solution is neutralised with aqueous ammonia solution and separated from the aqueous phase. The toluene solution is then concentrated until component A crystallises from the mixture of diastereoisomers of formula (11). A yield of 1.9 g of component A according to Example 1 is obtained after purification with isopropyl alcohol, filtration and drying.

Component B (0.6 g) is obtained by subjecting the filtrate to column chromatography.

EXAMPLE 4

With stirring, 2.5 g of sodium bicarbonate, 0.9 g of potassium iodide and 6.9 g of desyl chloride are added to 7.7 g of 2-amino-6-diethylaminofluoran in 100 ml of ethyl alcohol (95%). The mixture is heated to reflux temperature and kept at this temperature for 2 hours. Working up of the reaction product as described in Example 3 gives the mixture of diastereoisomers of formula (11), which is separated into components A and B having the properties described in Example 3.

EXAMPLE 5

7.7 g of 2-amino-6-diethylaminofluoran are suspended in 25 ml of tetrahydrofuran at 20°–25° C. with 5.4 g of phthalic acid and 3.9 g of desoxy benzoin (phenylbenzyl ketone). With stirring, 0.8 g of sodium borohydride are first strewn in over 50 minutes and the reaction mixture is then kept for 1½ hours at 50° C. Then 2 ml of acetic acid, 1 ml of water and 4.9 g of chloroanil are added, after which the reaction proceeds for 1 hour at 30°–40°

C. After addition of 100 ml of toluene and 100 ml of water the phase are separated and the toluene phase is concentrated, affording 6.5 g of a fluoran of formula

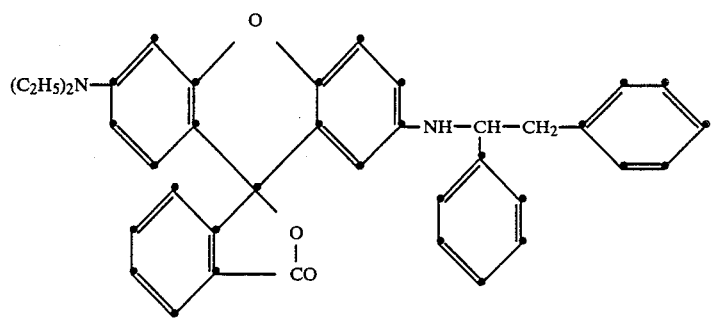

(12)

This fluoran is a mixture of diastereoisomers. It develops a black image immediately on acid-modified clay.

The mixture of diastereoisomers is separated into the individual components A ($R_f=0.61$) and B ($R_f=0.68$) by thin-layer chromatography on silica gel with toluene/ethyl acetate (1:1) as eluant. Recrystallisation from isopropyl alcohol gives 1.2 g of component A, m.p. 175°–176.5° C., and 0.7 g of component B, m.p. 227°–229° C.

Component A immediately develops a grey image on acid-modified clay and a greyish-green image on phenolic resin.

Component B immediately develops a grey image on acid-modified clay, and a greenish-grey image on phenolic resin.

EXAMPLE 6

With stirring, 3.8 g of sodium bicarbonate, 1.3 g of potassium iodide and 10.4 g of desyl chloride are added to 12 g of 2-amino-3-methyl-6-diethylaminofluoran in 150 ml of 95% ethyl alcohol. The mixture is heated, under nitrogen, to 55° C., and this temperature is kept for 6½ hours. To separate the mixture of diastereoisomers, the reaction product is isolated by filtration at 20° C., washed with isopropyl alcohol and water, and dried at 80° C. under vacuum, affording 9.5 g of a fluoran of formula To purify and separate the mixture, the crude product is dissolved hot in toluene, the solution is extracted with aqueous ammonia, and the separated toluene phase is concentrated until component A crystallises. The crystalline product is isolated by filtration and dried, affording 1.3 g of component A with a melting point of 251°–252° C.

Component A develops a black image immediately on phenolic resin.

To isolate component B, the filtrate obtained above is separated by column chromatography over silica gel with toluene and 20% ethyl acetate. The yield of component B is 1.4 g. The melting point is 146°–148° C. Component B develops a black image immediately on phenolic resin.

EXAMPLE 7

7.95 g of 2-amino-6-dibutylaminofluoran are added at 50° C. to 20 g of fused desoxybenzoin in 30 ml of tetrahydrofuran and to this mixture are added 8.4 g of phthalic acid. Then 1.45 g of sodium borohydride are added at 50°–55° C. over 1½ hours and the reaction mixture is stirred for 4½ hours at 60° C. After dilution with 30 ml of tetrahydrofuran, the batch is filtered and the filtrate is concentrated to dryness. The residue is taken up in 150 ml of 30% hydrochloric acid at 55° C. and the solution is extracted with 200 ml of toluene. The aqueous phase is neutralised with 30% sodium hydroxide solution and extracted with toluene. The toluene phase is then concentrated to dryness, affording 11.6 g of a fluoran of formula

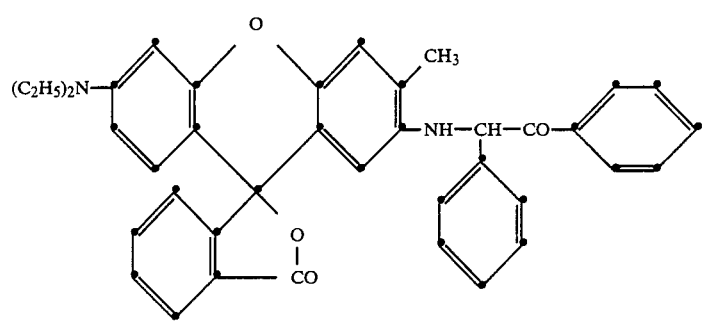

(13)

This fluoran a mixture of diastereoisomers. It develops a black image immediately on acid-modified clay.

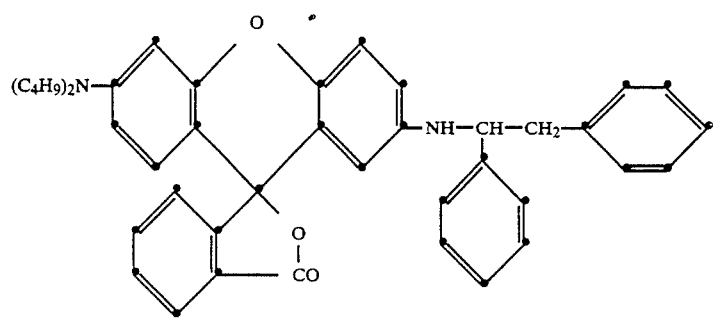

(14)

as a mixture of diastereoisomers. Two recrystallisations from isopropyl alcohol with 10% toluene give 2.7 g of the pure component A with a melting point of 205°–206° C. Component A develops an olive-grey image immediately on zinc salicylate.

The filtrate obtained from the above recrystallisation is separated into the individual fractions by column chromatography over silica gel with toluene and 10% ethyl acetate. After removal of the solvent, component B is obtained as amorphous substance in a yield of 1.4 g. Softening point: 66° C.

Component B develops an olive-grey image immediately on zinc salicylate.

The corresponding fluorans of formula

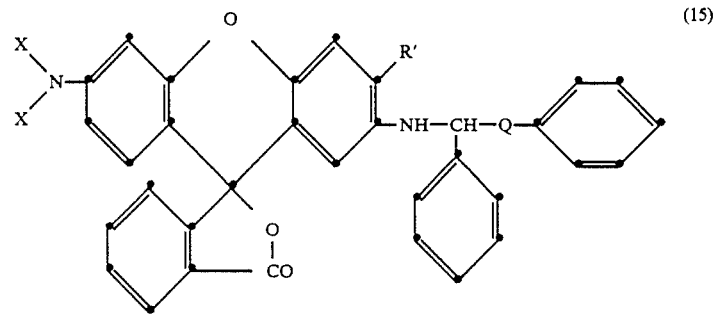

(15)

are obtained in the form of mixtures of diastereoisomers by using 2-amino-3-methyl-6-diethylaminofluoran, 2-amino-6-dibutylaminofluoran or 2-amino-3-methyl-6-dibutylaminofluoran in accordance with the procedures described in Examples 1 to 7. The separated diastereoisomer components A and B develop on acid clay the coloured images indicated in the following table.

Table

| Example | X | R' | Q | component A colour | component B colour |
|---|---|---|---|---|---|
| 8 | —$C_2H_5$ | —$CH_2$— | —$CH_2$— | grey | grey |

Table-continued

| Example | X | R' | Q | component A colour | component B colour |
|---|---|---|---|---|---|
| 9 | —$C_4H_9$ | H | —CO— | olive | olive |
| 10 | —n-$C_4H_9$ | —$CH_3$ | —CO— | grey | grey |
| 11 | —n-$C_4H_9$ | —$CH_3$ | —$CH_2$ | grey | grey |

EXAMPLE 12

To 11.6 g of 2-amino-6-diethylaminofluoran in 20 ml of tetrahydrofuran are added 7.5 g of phthalic acid and 36 g of ω-phenoxyacetophenone at 45°–50° C. Then 1.25 g of sodium borohydride are added in small portions at 50°–55° C. over a period of 2¼ hours. The reaction mixture is kept for 5 hours at 58°–60° C. and, after the addition of a further 50 ml of tetrahydrofuran, stirred for 15 hours at 20°–25° C. The reaction solution is clarified by filtration and, after the addition of 1 g of chloroanil, decolourised with aqueous ammonia and concentrated to dryness. The residue is taken up in 150 ml of 30% hydrochloric acid and extracted with toluene at 80°–85° C. The aqueous phase is adjusted to pH 12 with aqueous sodium hydroxide solution and extracted with toluene. After removal of the toluene, the toluene phase gives 9.1 g of a fluoran of formula

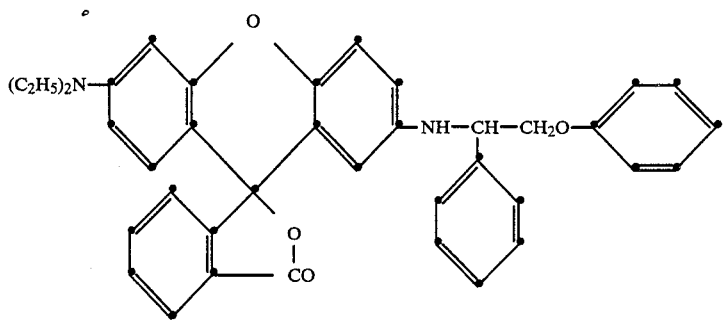
(16)

in the form of a mixture of diastereoisomers. Recrystallisation from toluene gives 1.7 g of component A with a melting point of 193°–194.5° C. Component A immediately develops a grey image on acid-modified clay and a greenish-grey image of very good lightfastness on phenolic resin.

The filtrate of the recrystallisation stage is subjected to column chromatography over silica gel with a 9:1 mixture of toluene/ethyl acetate as eluant, affording 1.6 g of component B with a melting point of 160°–161° C. Component B develops a lightfast grey image on acid-modified clay and on phenolic resin.

EXAMPLE 13

Preparation of a Pressure-sensitive Copying Paper

A solution of 3 g of the fluoran of formula (11) obtained in Example 1 in 80 g of diisopropylnaphthalene and 17 g of kerosene are microencapsulated by coacervation in a manner known per se with gelatin and gum arabic. The microcapsules are mixed with starch solution and coated on a sheet of paper. The face of a second sheet of paper is coated with activated clay as colour developer. The first sheet containing the colour former and the sheet coated with the developer are laid on top of each other with the coated sides face to face. Pressure is exerted on the first sheet by writing by hand or typewriter and a strong grey copy develops immediately on the sheet coated with the developer. This copying material has excellent fastness to sublimation.

Example 14

1 g of component A of the fluoran of formula (11) obtained in Example 1 is dissolved in 17 g of toluene. With stirring, 12 g of polyvinyl acetate, 8 g of calcium carbonate and 2 g of titanium dioxide are added to this solution. The resultant suspension is diluted with toluene in the weight ratio 1:1 and applied to a sheet of paper with a knife to a thickness of 10 μm. On this sheet of paper is laid a second sheet, the underside of which has been coated to a weight of 3 g/m² with a mixture consisting of 1 part of an amide wax, 1 part of a stearin wax and 1 part of zinc chloride. Pressure is exerted on the top sheet by writing by hand or typewriter and a strong grey copy develops immediately on the sheet coated with the colour former.

EXAMPLE 15

Preparation of a Heat-sensitive Recording Material

In a ball mill, 32 g of 4,4′-isopropylidenediphenol (bisphenol A), 3.8 g of the distearylamide of ethylenediamine, 39 g of kaolin, 20 g of an 88% hydrolysed polyvinyl alcohol and 500 ml of water are ground to a particle size of about 5 μm. In a second ball mill, 6 g of the fluoran obtained in Example 1, 3 g of a 88% hydrolysed polyvinyl alcohol and 60 ml of water are ground to a particle size of about 3 μm. Both dispersions are mixed and applied to paper to a dry coating weight of 5.5 g/m². A strong grey image of excellent lightfastness is produced by contacting the paper with a heated metal stylus.

What is claimed is:

1. A fluoran of the formula

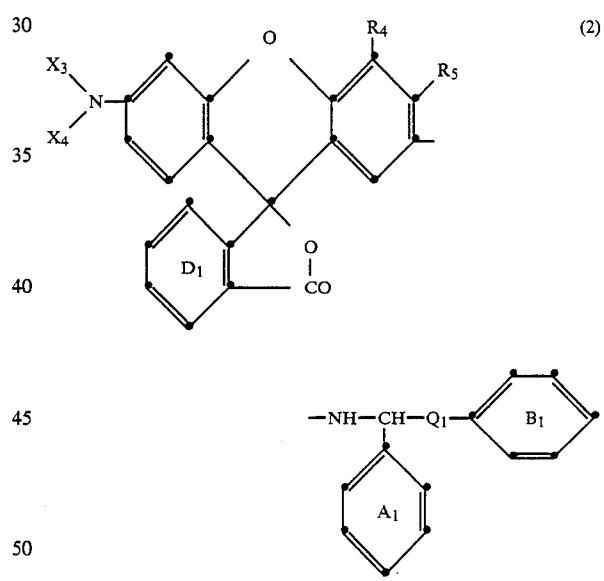

(2)

wherein
$Q_1$ is —CO—,
$R_4$ and $R_5$ are each independently of the other hydrogen, halogen or lower alkyl,
$X_3$ is $C_1$–$C_6$alkyl, $C_5$–$C_6$cycloalkyl, benzyl, phenyl or phenyl which is substituted by halogen, $C_1$–$C_4$alkyl or $C_1$–$C_4$alkoxy,
$X_4$ is $C_1$–$C_6$alkyl or benzyl, and wherein the benzene rings $A_1$ and $B_1$ are each independently of the other unsubstituted or substituted by halogen, lower alkyl or lower alkoxy, and the ring $D_1$ is unsubstituted or substituted by halogen.

2. A fluoran according to claim 1, wherein $X_3$ and $X_4$ are $C_1$–$C_4$alkyl, $R_4$ and $R_5$ are hydrogen, methyl or chloro, and the rings $A_1$, $B_1$ and $D_1$ are unsubstituted.

3. A fluoran of the formula

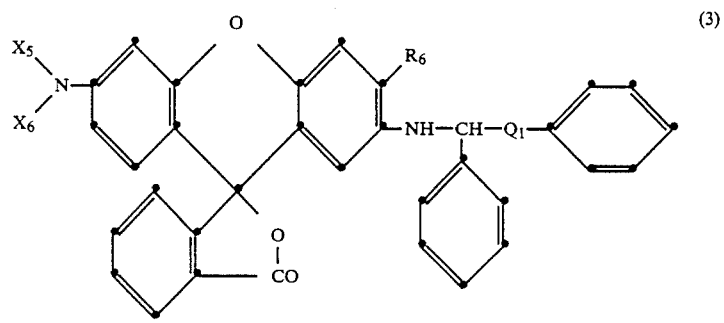
(3)
wherein
$Q_1$ is —CO—,
$R_6$ is hydrogen or methyl,
$X_5$ is $C_1$-$C_4$alkyl, cyclohexyl or tolyl, and
$X_6$ is $C_1$-$C_4$alkyl.
4. The fluoran of claim 3, wherein $R_6$ is hydrogen, and $X_5$ and $X_6$ are ethyl.
5. The fluoran of claim 3, wherein $R_6$ is hydrogen, and $X_5$ and $X_6$ are butyl.
6. The fluoran of claim 3, wherein $R_6$ is methyl and $X_5$ and $X_6$ are ethyl.
* * * * *